United States Patent
Funke et al.

(10) Patent No.: US 6,548,704 B2
(45) Date of Patent: Apr. 15, 2003

(54) RACEMIZATION OF OPTICALLY ACTIVE AMINES

(75) Inventors: Frank Funke, Mannheim (DE); Shelue Liang, Ludwigshafen (DE); Andreas Kramer, Bad Dürkheim (DE); Rainer Stürmer, Rödersheim-Gronau (DE); Arthur Höhn, Kirchheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/012,344

(22) Filed: Dec. 12, 2001

(65) Prior Publication Data

US 2002/0120166 A1 Aug. 29, 2002

(30) Foreign Application Priority Data

Dec. 15, 2000 (DE) ......................... 100 62 729

(51) Int. Cl.$^7$ .............................. C07C 29/68
(52) U.S. Cl. ........................................ 564/302
(58) Field of Search .......................... 564/302

(56) References Cited

U.S. PATENT DOCUMENTS

| | | | |
|---|---|---|---|
| 3,954,870 A | | 5/1976 | Fukumaru |
| 4,096,186 A | | 6/1978 | Ichikawa |
| 4,246,424 A | * | 1/1981 | Nagase et al. ............. 560/38 |
| 4,990,666 A | | 2/1991 | Harsy |
| 6,049,007 A | * | 4/2000 | Riechers et al. ........... 564/302 |
| 6,060,624 A | * | 5/2000 | Hayes et al. ............... 564/302 |
| 6,153,797 A | | 11/2000 | Riechers |
| 6,160,178 A | | 12/2000 | Riechers |

FOREIGN PATENT DOCUMENTS

| | | |
|---|---|---|
| DE | 28 51 039 | 6/1980 |
| DE | 29 03 598 | 8/1980 |
| WO | 00/29357 | 3/2000 |
| WO | 00/47545 | 8/2000 |
| WO | 00/47546 | 8/2000 |

OTHER PUBLICATIONS

Chem.Abst. 110:192247v, 1988.
Derwent Abst. 94–197043/24, 1994.
Patent Abst. of Japan, vol. 12, No. 467 (C550), 1987.

* cited by examiner

*Primary Examiner*—Brian Davis
(74) *Attorney, Agent, or Firm*—Keil & Weinkauf

(57) ABSTRACT

Optically active amines of the formula I

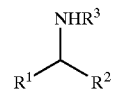

(I)

where $R^1$ and $R^2$ are different and $R^1$, $R^2$, $R^3$ are alkyl, cycloalkyl, arylalkyl, aryl, heteroaryl and heterocyclic radicals and $R^3$ may also be hydrogen (H), with the radicals being able to bear substituents selected from the group consisting of alkyl, cycloalkyl, alkoxy, aryloxy, amino, alkylamino and dialkylamino, are racemized by reacting the optically active amine I in the presence of hydrogen and a hydrogenation or dehydrogenation catalyst at elevated temperature, wherein the catalyst comprises the active components copper and zinc oxide and a support material.

15 Claims, No Drawings

RACEMIZATION OF OPTICALLY ACTIVE AMINES

The present invention relates to a process for racemizing optically active amines of the formula I

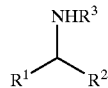

(I)

where $R^1$ and $R^2$ are different and $R^1$, $R^2$, $R^3$ are alkyl, cycloalkyl, arylalkyl, aryl, heteroaryl and heterocyclic radicals and $R^3$ may also be hydrogen (H), with the radicals being able to bear substituents selected from the group consisting of alkyl, cycloalkyl, alkoxy, aryloxy, amino, alkylamino and dialkylamino, by reacting the optically active amine I in the presence of hydrogen and a hydrogenation or dehydrogenation catalyst at elevated temperature.

Optically active amines of the formula I are, for example, valuable pharmaceuticals and intermediates for the preparation of active compounds (cf., for example: DE-A-29 03 589, page 2, lines 17 to 26). Since frequently only one of the two enantiomers (based on the asymmetric carbon atom shown in the formula I) is active, or is more active than the other enantiomer, processes are required for racemizing the less active enantiomer which is obtained, for example, in resolution of the corresponding racemic amine by known methods, because the more active enantiomer can once again be obtained from the racemized amine by known methods (e.g. resolution).

Chem. Abstracts 110: 192247v (IN-A-162 213) discloses a process for preparing racemic 2-aminobutanol by treating 1-2-aminobutanol with ammonia in the presence of $Rh/Al_2O_3$.

U.S. Pat. No. 4,096,186 describes a process for racemizing optically active amino alcohols in which the amino alcohol is brought into contact with ammonia and hydrogen in the presence of a hydrogenation catalyst which preferably comprises cobalt. In the reaction of optically active 2-amino-1-butanol, a degree of racemization of only 63% is achieved at a racemate yield of at most 97.6%. At a degree of racemization of 99%, on the other hand, a racemate yield of only 75.1% is achieved.

U.S. Pat. No. 4,990,666 discloses a process for racemizing optically active amino alcohols in which the amino alcohol is brought into contact with Raney cobalt in the presence of hydrogen. It is stated that high temperatures, e.g. above 160° C., reduce the racemate yield.

Derwent Abstract No. 94-197043/24 (Chem. Abstracts 121: 179093z; JP-A-06 135 906) describes a process for racemizing optically active vicinal primary diamines in the presence of hydrogen and a hydrogenation catalyst such as Raney nickel and Raney cobalt.

Patent Abstracts of Japan, Vol. 12, No. 467 (C-550), (JP-A-63 185 943), describes the racemization of optically active 1-methyl-3-phenylpropylamine in the presence of Raney nickel or Raney cobalt and hydrogen at 50–200° C.

U.S. Pat. No. 3,954,870 discloses a method of racemizing certain optically active alpha,beta-diphenylethylamines by heating in the presence of dry Raney nickel.

DE-A-28 51 039 describes a process for preparing racemic mixtures from optically active 1-arylamines in which the optically active 1-arylamines are treated with hydrogen in the presence of a hydrogenation catalyst, in particular Raney cobalt.

DE-A-29 03 589 describes a process for preparing racemic mixtures from optically active amines by treating the optically active amines with hydrogen at elevated temperature in the presence of a hydrogenation catalyst, in particular Raney cobalt or Raney nickel. The reaction of optically active 2-amino-1-phenylpropane over a Raney cobalt catalyst for a reaction time of 12 hours leads, at a degree of racemization of at most 98%, to a racemate yield of only 91.1%.

WO 00/29357 relates to a process for racemizing optically active amines by reaction of the optically active amine in the gas phase in the presence of hydrogen and a hydrogenation or dehydrogenation catalyst at elevated temperature.

WO 00/47546 discloses a process for racemizing optically active amines by reaction of the optically active amine in the presence of hydrogen and a hydrogenation or dehydrogenation catalyst at elevated temperature, in which the reaction is carried out in the liquid phase and the catalyst comprises the catalytically active constituents copper, silver, iron, cobalt, nickel, ruthenium, rhodium, palladium, osmium, iridium and/or platinum and a support material selected from the group consisting of aluminum oxide, zirconium dioxide, titanium dioxide, carbon and oxygen-containing compounds of silicon.

WO 00/47545 (equivalent: U.S. Pat. No. 6,049,007) describes a process for preparing racemic amines by simultaneously reacting a corresponding optically active amine and a corresponding secondary alcohol and/or a corresponding unsymmetrical ketone and a particular amine in situ in the presence of hydrogen and a hydrogenation or dehydrogenation catalyst at elevated temperature.

U.S. Pat. No. 6,060,624 relates to a process for racemizing particular optically active primary β-alkoxyalkylamines by reaction over a nickel or cobalt catalyst in the presence of hydrogen and ammonia.

Another disadvantage of some processes of the prior art is that expensive noble metal catalysts are used.

It is an object of the present invention to discover an improved economical process for racemizing optically active amines in which the process product is obtained with a high degree of racemization at a simultaneously high racemization yield (racemate yield) and a high space-time yield.

We have found that this object is achieved by a process for racemizing optically active amines of the formula I

(I)

where $R^1$ and $R^2$ are different and $R^1$, $R^2$, $R^3$ are alkyl, cycloalkyl, arylalkyl, aryl, heteroaryl and heterocyclic radicals and $R^3$ may also be hydrogen (H), with the radicals being able to bear substituents selected from the group consisting of alkyl, cycloalkyl, alkoxy, aryloxy, amino, alkylamino and dialkylamino, by reacting the optically active amine I in the presence of hydrogen and a hydrogenation or dehydrogenation catalyst at elevated temperature, wherein the catalyst comprises the active components copper and zinc oxide and a support material.

In a particular embodiment, the catalyst comprises an oxidic support material selected from the group consisting of aluminum oxide, silicon dioxide, titanium dioxide, zirconium dioxide, magnesium oxide, iron oxide and cerium dioxide or carbon or mixtures thereof.

Aluminum oxide is preferred as support material.

The process of the present invention can be carried out in the liquid phase or preferably in the gas phase, batchwise or preferably continuously, as follows, with the catalyst preferably being present in the reactor as a fixed bed.

The process of the present invention can be carried out in the absence or preferably the presence of the amine of the formula $R^3NH_2$ in which the radical $R^3$ corresponds to the radical $R^3$ of the optically active amine I (e.g. the amine ammonia in the case of racemization of optically active amines I in which $R^3$=H).

If the process is carried out in the presence of the amine $R^3NH_2$, the molar ratio of $R^3NH_2$ to amine I is generally from 1:1 to 50:1, preferably from 1.5:1 to 30:1, particularly preferably from 2:1 to 20:1, very particularly preferably from 2:1 to 10:1. The $R^3NH_2$ excess based on the amine I can also be greater than 50:1.

The hydrogen is generally fed into the reaction in an amount of from 5 to 400 l, preferably from 10 to 200 l, per mole of amine component I, with the number of liters quoted being based on S.T.P. in each case.

When the process of the present invention is carried out in the gas phase, the optically active amine I is continuously passed in gaseous form in a gas stream which is sufficiently large for vaporization and comprises hydrogen and advantageously the amine $R^3NH_2$, preferably consists of hydrogen and the amine $R^3NH_2$, over the catalyst at pressures of generally from 0.1 to 30 MPa, in particular from 0.1 to 10 MPa, preferably from 0.1 to 5 MPa, particularly preferably from 0.1 to 3 MPa, in a reactor, e.g. an externally heated tube reactor.

The gaseous mixture can be passed through the fixed catalyst bed either from the top or from the bottom. The gas stream required is preferably obtained by means of circulating gas operation, with, for example, a circulating gas flow of from about 5 to 10 m³/h (volume converted to S.T.P.) and an off-gas flow of from about 250 to 350 l/h being employed at a catalyst bed volume of 1 l. The weight hourly space velocity over the catalyst is generally in the range from 0.1 to 2, preferably from 0.1 to 1, particularly preferably from 0.3 to 0.8, kg of amine I per liter of catalyst (bed volume) and hour.

The racemization of the optically active amine I in the gas phase can be carried out in the presence of an inert diluent which is gaseous under the reaction conditions chosen, for example nitrogen and/or argon.

When the process of the present invention is carried out in the liquid phase, the optically active amine I is passed in liquid form over the catalyst, which is usually located in a preferably externally heated fixed-bed reactor, e.g. tube reactor, in the presence of hydrogen and advantageously the amine $R^3NH_2$ at pressures of from 0.1 to 30 MPa, preferably from 5 to 25 MPa, particularly preferably from 10 to 25 MPa.

When the racemization is carried out in a tube reactor, the reaction mixture can be passed through the fixed catalyst bed from the top (downflow mode) or from the bottom (upflow mode). Operation using circulating gas is advantageous, with, for example, a circulating gas flow of from about 0.01 to 1 m³/h (volume converted to S.T.P.) and an off-gas flow of from about 10 to 300 l/h being employed at a catalyst bed volume of 1 l.

The weight hourly space velocity over the catalyst is generally in the range from 0.05 to 2, preferably from 0.1 to 1, particularly preferably from 0.2 to 0.6, kg of amine I per liter of catalyst (bed volume) and hour.

The temperatures selected for the racemization in the liquid phase and in the gas phase are in the range from 100 to 300° C., preferably from 150 to 270° C., particularly preferably from 160 to 250° C., very particularly preferably from 170 to 240° C., in particular from 180 to 230° C.

The racemization of the optically active amine I in the liquid phase can be carried out in the presence of an inert diluent or solvent which is liquid under the reaction conditions chosen, for example tetrahydrofuran, dioxane, N-methylpyrrolidone and/or ethylene glycol dimethyl ether.

The use of temperatures, total pressures or weight hourly space velocities over the catalyst higher than those indicated above is also possible both when the process is carried out in the gas phase and when it is carried out in the liquid phase.

The pressure in the reaction vessel, which is essentially the sum of the partial pressures of the optically active amine I, the amine $R^3NH_2$ if present, the racemized amine I formed and any diluent or solvent present at the particular temperature employed, is advantageously increased to the desired reaction pressure by injection of hydrogen.

In a particular embodiment of the process for racemizing optically active amines of the formula I, the reaction is carried out in the presence of the amine of the formula $R^3NH_2$ in which the radical $R^3$ corresponds to the radical $R^3$ of the optically active amine I, and the secondary alcohol of the formula II and/or the unsymmetrical ketone of the formula III

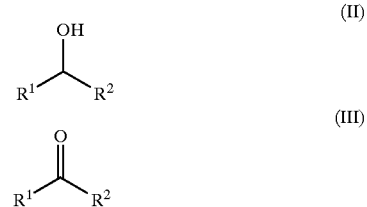

in which the radicals $R^1$ and $R^2$ correspond to the radicals $R^1$ and $R^2$ of the amine I, are/is reacted simultaneously in situ to form the racemic amine I.

This particular process variant can be illustrated by the following reaction scheme:

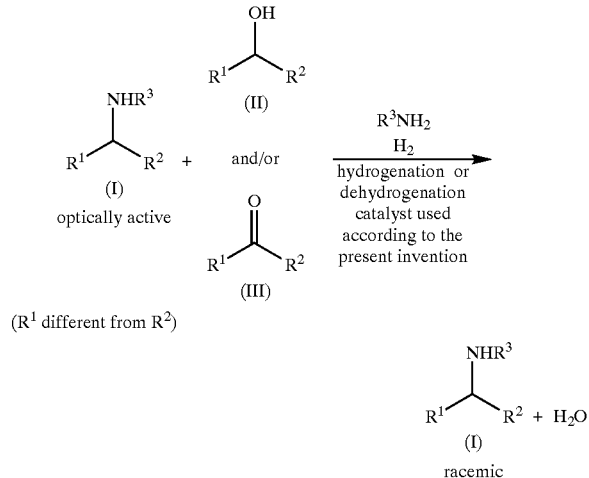

In general, the molar ratio of $R^3NH_2$ to the sum of optically active amine I and alcohol II and/or ketone III is from 1:1 to 50:1, preferably from 1.5:1 to 30:1, particularly preferably from 2:1 to 20:1, very particularly preferably from 2:1 to 10:1. The molar excess of $R^3NH_2$ based on the sum of optically active amine I and alcohol II and/or ketone III can also be greater than 50:1.

The molar ratio of optically active amine I to alcohol II and/or ketone III is not critical and can be varied within a wide range; it is generally from 1:100 to 100:1, preferably from 1:50 to 50:1, for example 1:1.

The hydrogen is generally used in the reaction in an amount of from 5 to 400 l, preferably from 10 to 200 l, per molar sum of optically active amine I and alcohol II and/or ketone III, with the number of liters quoted being based on S.T.P. in each case.

Otherwise, this particular process variant is carried out in the liquid phase or preferably in the gas phase as described above, with the secondary alcohol of the formula II and/or the unsymmetrical ketone of the formula III being used in addition to the optically active amine I. In this case, the weight hourly space velocities over the catalyst indicated above in kg per liter of catalyst and hour refer to the starting material mixture [amine+(alcohol and/or ketone)].

The output from the reactor is advantageously depressurized and then subjected to a separation step (e.g. a distillation) to remove hydrogen, any amine of the formula $R^3NH_2$ used and any diluent or solvent used, with these being able to be recirculated, and the cooled crude reaction product obtained, which consists essentially of racemic amine I, is purified by fractional rectification at atmospheric pressure or under reduced pressure.

In the case of the above-described particular process variant in which the secondary alcohol of the formula II and/or the unsymmetrical ketone of the formula III are/is reacted simultaneously in situ, the crude reaction product additionally contains water. The water is preferably removed by treatment with aqueous sodium hydroxide having a concentration of about 50% before the rectification is carried out.

The process of the present invention can be used, for example, for preparing racemic 1-methoxy-2-aminopropane ((R,S)-MOIPA) ($R^1$=—$CH_3$, $R^2$=—$CH_2OCH_3$, $R^3$=H).

According to the above-described particular process variant, the preparation of racemic MOIPA, for example, can be carried out by simultaneous in-situ reaction of optically active 1-methoxy-2-aminopropane, 1-methoxy-2-propanol and ammonia according to the process of the present invention.

The work-up of the crude process product obtained according to this example, which consists essentially of (R,S)-MOIPA and water, can be carried out, for example, by admixing the crude product with aqueous sodium hydroxide, separating off the aqueous phase and distilling the (R,S)-MOIPA-containing phase, as described in EP-A-881 211.

The additional advantage of the above-described particular variant of the process of the present invention is, inter alia, its particularly good economics, since it is not necessary to construct separate plants for preparing the racemic amines I by (a) amination of secondary alcohols II or unsymmetrical ketones III with amines of the formula $R^3NH_2$ and (b) racemization of the corresponding optically active amine I, but instead the processes (a) and (b) can be carried out simultaneously in situ. (On this subject, see also page 1 of the description, 2nd paragraph).

Surprisingly, combining the two completely different process steps (a) and (b) mentioned above into a single process has virtually no influence on the yields and selectivities of the individual process steps, i.e. there is virtually no increased formation of by-products such as symmetrical amines of the formula

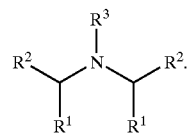

It is recognized according to the present invention that the use of nickel or cobalt catalysts in the above-described particular process variant can be critical, since these catalysts can easily convert the alcohols II or ketones III to be aminated into methane or ethane (as cleavage products) ("cleavage reaction"). The formation of these cleavage products not only reduces the yields of racemic amine I but can also, in the case of uncontrolled, increased cleavage, especially in an adiabatically operated reactor, cause a dangerous, exothermic runaway reaction which can lead to temperatures above 500° C. in the reactor. According to the invention, the catalysts found firstly display a low tendency to catalyze cleavage reactions (as described above) in the amination of alcohols II or ketones III even at high temperatures and at the same time give the above-described advantages of the racemization process of the present invention (e.g. high degree of racemization together with high yield of racemic amine I).

The catalysts used in the process of the present invention comprise the active components copper and zinc oxide and a support material.

The catalysts can be used either in powder form in suspension or preferably in the form of all-active catalysts, impregnated catalysts, coated catalysts or precipitated catalysts in a fixed bed.

Support materials used are oxides of the elements aluminum, silicon, zirconium, titanium, magnesium, iron or cerium or carbon or mixtures of these support materials.

Examples of such oxides are $Al_2O_3$, $SiO_2$, $ZrO_2$, $TiO_2$, MgO, $Fe_2O_3$ (e.g. magnetite), $CeO_2$. Carbon can be used in the form of activated carbon as support material.

Aluminum oxide ($Al_2O_3$) is used, for example, in the form of α-, β-, γ- or θ-$Al_2O_3$ or D10-10 from BASF.

A particularly preferred support material is a mixture of aluminum oxide and zinc oxide.

In a very particularly preferred embodiment, the catalyst further comprises zinc-aluminum spinel. On this subject, see, for example, U.S. Pat. No. 3,923,694, where such a catalyst is disclosed.

There are no particular restrictions in respect of the preparation of the support material.

In general, the oxidic support material can be prepared, for example, by precipitation of an aqueous solution comprising zinc nitrate and an appropriate metal salt, e.g. aluminum nitrate, with sodium carbonate and subsequent filtration, drying and optionally calcination of the precipitate obtained in this way.

To produce the catalyst used in the process of the present invention, the active components copper and zinc oxide are applied to the abovementioned support material, with the method of application being subject to no restrictions.

In particular, a copper salt solution and a zinc salt solution or a solution comprising copper and zinc salts can be applied in one or more impregnation steps to the prefabricated support in the form of powder, spheres, extrudates or pellets. After impregnation, the support is dried and, if appropriate, calcined.

Such impregnation methods are described, for example, in EP-A-599 180, EP-A-673 918 or A. B. Stiles, Catalyst Manufacture—Laboratory and Commercial Preparations, Marcel Dekker, pages 89 to 91, New York (1983).

A copper salt solution and a zinc salt solution or a solution comprising copper and zinc salts can also be applied by precipitation to the prefabricated support, which in a particularly preferred embodiment is present as powder in an aqueous suspension. Precipitation is carried out by methods known in the prior art.

The precipitates obtained in the precipitation process are filtered off in a customary manner and preferably washed free of alkali, as described, for example, in DE-A-198 09 418, dried at from 50 to 150° C., preferably at about 120° C., and subsequently calcined if appropriate, generally at from 200 to 600° C., in particular from 300 to 500° C., preferably for about 2 hours.

As starting materials for production of the catalyst, it is in principle possible to use all Cu(I) and/or Cu(II) salts which are soluble in the solvents used in the application, for example nitrates, carbonates, acetates, oxalates or ammonium complexes, and analogous Zn(II) salts. Particular preference is given to using copper nitrate and zinc nitrate.

For the process of the present invention, the above-described dried and preferably calcined catalyst powder is preferably processed to form pellets, rings, annular tablets, extrudates, honeycombs or similar shaped bodies. All methods known from the prior art can be employed for this purpose.

Preferred catalysts comprise, after drying and before activation with a reducing agent (for reducing agents, see below), from 20 to 90% by weight, in particular from 40 to 85% by weight, very particularly preferably from 60 to 80% by weight, of oxygen-containing compounds of copper, calculated as CuO, from 9 to 60% by weight, in particular from 13 to 40% by weight, very particularly preferably from 17 to 30% by weight, of oxygen-containing compounds of zinc, calculated as ZnO, and a total of from 1 to 60% by weight, in particular from 2 to 35% by weight, very particularly preferably from 3 to 10% by weight, of the above-mentioned oxidic support materials, in each case calculated as $Al_2O_3$, $SiO_2$, $ZrO_2$, $TiO_2$, MgO, $Fe_2O_3$ or $CeO_2$, in particular aluminum oxide (calculated as $Al_2O_3$), in each case based on the total weight of all oxidic constituents of the catalyst, with catalyst shaping aids (cements) not being included in the oxidic constituents.

Particularly preferred catalysts comprise, after drying and before activation with a reducing agent, the constituents oxygen-containing compounds of copper, oxygen-containing compounds of zinc and abovementioned oxidic support material, in particular aluminum oxide, in a combined amount of at least 80% by weight, in particular at least 90% by weight, based on the total weight of all oxidic constituents of the catalyst, with catalyst shaping aids (cements) not being included in the oxidic constituents.

In particular catalyst embodiments, the catalyst after drying and before activation with a reducing agent further comprises from 0.01 to 10% by weight, preferably from 0.01 to 5% by weight, for example from 1 to 10% by weight and preferably from 1 to 5% by weight, in each case based on the total weight of all oxidic constituents of the catalyst (with the catalyst shaping aids (cements) not being included in the oxidic constituents), of at least one additional component selected from the group consisting of oxides of the elements Re, Fe, Ru, Co, Rh, Ir, Ni, Pd and Pt.

These components can likewise be introduced into the catalyst material via the known precipitation or impregnation methods.

In this particular catalyst embodiment, the catalyst after drying and before activation with a reducing agent comprises from 20 to 89% by weight, in particular from 40 to 84% by weight, very particularly preferably from 60 to 79% by weight, of oxygen-containing compounds of copper, calculated as CuO, based on the total weight of all oxidic constituents of the catalyst (with catalyst shaping aids (cements) not being included in the oxidic constituents).

In the production of shaped bodies of the catalysts used in the process of the present invention, it is possible to add pulverulent copper or pulverulent catalyst shaping aid (cement) or a mixture thereof as additive prior to shaping the catalyst material so as to improve catalyst performance (higher activity, selectivity, mechanical and chemical stability).

In general, pulverulent copper or pulverulent cement or a mixture thereof can be added to the catalyst material in an amount of from 1 to 40% by weight, preferably from 2 to 20% by weight and particularly preferably from 5 to 10% by weight, in each case based on the total weight of all oxidic constituents of the catalyst material.

Examples of catalyst shaping aids (cements) are stearic acid and graphite.

In a preferred embodiment, copper powder and cement powder having a particle size distribution in which at least 45%, preferably at least 70%, particularly preferably at least 90% (figures quoted in % by weight), of the copper or cement particles have particle sizes in the range from 10 to 100 mm are used. The surface area of the copper powder or cement powder used, determined by the BET method, is generally in the range from 0.01 to 20 $m^2/g$, preferably in the range from 0.05 to 10 $m^2/g$, particularly preferably in the range from 0.1 to 0.5 $m^2/g$.

In a further preferred embodiment, graphite is added as shaping aid to the catalyst material in addition to the copper powder or the cement powder or the mixture thereof in the production of shaped bodies of the catalysts used in the process of the present invention so as to improve catalyst performance (see above). Graphite is preferably added in such an amount that the shaping to produce a shaped body can be carried out better and more easily. For example, from 0.5 to 5% by weight of graphite, based on the total weight of all oxidic constituents of the catalyst material, are added. It is immaterial whether graphite is added to the catalyst material before or after or simultaneously with the copper powder or the cement powder or the mixture thereof.

After addition of the copper powder or the cement powder or the mixture thereof and optionally the graphite to the catalyst material, the shaped catalyst body obtained after shaping may be calcined at least once, for a time of generally from 0.5 to 10 hours, preferably from 0.5 to 2 hours. The temperature in this/these calcination step(s) is generally in the range from 200 to 600° C., preferably in the range from 250 to 500° C. and particularly preferably in the range from 300 to 400° C.

When used as catalyst in the oxidic form, the shaped body is generally prereduced by means of reducing gases, for example hydrogen, preferably hydrogen/inert gas mixtures, in particular hydrogen/nitrogen mixtures, at from 100 to 500° C., preferably from 150 to 350° C. and in particular from 180 to 200° C., (activation) prior to being supplied with the amine I to be racemized. In this activation, preference is given to using a mixture having a proportion of hydrogen in the range from 1 to 100% by volume, particularly preferably in the range from 1 to 50% by volume.

In a preferred embodiment, the shaped catalyst body is activated in a manner known per se by treatment with reducing media before it is used. Activation is carried out either beforehand in a reduction oven or after installation in the reactor. If the catalyst has been activated beforehand in a reduction oven, it is installed in the reactor and supplied directly under hydrogen pressure with the amine I to be racemized.

The radicals $R^1$, $R^2$ and $R^3$, with $R^1$ and $R^2$ being different, are, independently of one another, alkyl, cycloalkyl, arylalkyl, aryl, heteroaryl and heterocyclic radicals and $R^3$ may also be hydrogen (H), with the radicals being able to bear substituents selected from the group consisting of alkyl, cycloalkyl, alkoxy, aryloxy, amino, alkylamino and dialkylamino which are inert under the reaction conditions.

$R^1$, $R^2$ and $R^3$ are each preferably:

- a linear or branched alkyl radical such as $C_{1-20}$-alkyl, particularly preferably $C_{1-12}$-alkyl, for example methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, cyclopentylmethyl, n-heptyl, isoheptyl, cyclohexylmethyl, n-octyl, 2-ethylhexyl, n-nonyl, isononyl, n-decyl, isodecyl, n-undecyl, n-dodecyl, isododecyl, very particularly preferably $C_{1-8}$-alkyl such as methyl, ethyl, n-propyl, isopropyl, n-butyl, isobutyl, sec-butyl, tert-butyl and 2-ethylhexyl,

- a cycloalkyl radical, preferably $C_{3-8}$-cycloalkyl, such as cyclopropyl, cyclobutyl, cyclopentyl, cyclohexyl, cycloheptyl and cyclooctyl, particularly preferably cyclopentyl, cyclohexyl and cyclooctyl, very particularly preferably cyclopentyl and cyclohexyl,

- an arylalkyl radical, preferably $C_{7-20}$-arylalkyl such as benzyl, 1-phenethyl, 2-phenethyl, 1-naphthylmethyl, 2-naphthylmethyl, phenanthrylmethyls, 4-tert-butylphenylmethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl,

- an aromatic radical, preferably $C_{6-20}$-aryl such as phenyl, 1-naphthyl, 2-naphthyl, 1-anthryl, 2-anthryl, 9-anthryl, particularly preferably phenyl, 1-naphthyl and 2-naphthyl, very particularly preferably phenyl,

- a heteroaromatic radical, preferably $C_{3-15}$-heteroaryl such as 2-pyridinyl, 3-pyridinyl, 4-pyridinyl, quinolinyl, pyrazinyl, pyrrol-3-yl, thienyl, imidazol-2-yl, 2-furanyl and 3-furanyl, or

- a heterocyclic radical, preferably $C_{3-15}$-heterocycloalkyl such as N-alkylpiperidin-3-yl, N-alkylpiperidin-4-yl, N,N'-dialkylpiperazin-2-yl, tetrahydrofuran-3-yl and N-alkylpyrrolidin-3-yl, where in these cases the radicals R may, independently of one another, bear substituents which are inert under the reaction conditions, for example $C_{1-20}$-alkyl, $C_{3-8}$-cycloalkyl, $C_{1-20}$-alkoxy, $C_{6-20}$-aryloxy, amino, $C_{1-20}$-alkylamino and $C_{2-20}$-dialkylamino.

The number of these substituents in R can be, depending on the type of radical, from 0 to 5, preferably from 0 to 3, in particular 0, 1 or 2. Possible substituents are, in particular:

$C_{1-20}$-alkyl as defined above, $C_{3-8}$-cycloalkyl as defined above, $C_{1-20}$-alkoxy, preferably $C_{1-8}$-alkoxy, for example methoxy, ethoxy, n-propoxy, isopropoxy, n-butoxy, isobutoxy, sec-butoxy, tert-butoxy, n-pentoxy, isopentoxy, sec-pentoxy, neopentoxy, 1,2-dimethylpropoxy, n-hexoxy, isohexoxy, sec-hexoxy, n-heptoxy, isoheptoxy, n-octoxy, isooctoxy, particularly preferably $C_{1-4}$-alkoxy such as methoxy, ethoxy, n-propoxy, isopropoxy, n-butoxy, isobutoxy, sec-butoxy and tert-butoxy, $C_{6-20}$-aryloxy such as phenoxy, 1-naphthoxy and 2-naphthoxy, preferably phenoxy, amino (—NH$_2$), $C_{1-20}$-alkylamino, preferably $C_{1-12}$-alkylamino, particularly preferably $C_{1-8}$-alkylamino such as methylamino, ethylamino, n-propylamino, isopropylamino, n-butylamino, isobutylamino, tert-butylamino, cyclopentylamino, cyclohexylamino, and $C_{2-20}$-dialkylamino, preferably $C_{2-12}$-dialkylamino, particularly preferably $C_{2-8}$-dialkylamino, such as N,N-dimethylamino, N,N-diethylamino, N,N-di-n-propylamino, N,N-diisopropylamino, N,N-Di-n-butylamino, N-ethyl-N-methylamino, N-methyl-N-propylamino, dicyclohexylamino.

$R^3$ is very particularly preferably hydrogen (H).

Examples of amines I which can be used in the process of the present invention are:

1-methoxy-2-aminopropane (MOIPA), 2-amino-3-methylbutane, 2-amino-3,3-dimethylbutane, 1-phenylethylamine, 1-naphthylethylamine, 2-naphthylethylamine, 1-phenylpropylamine, 2-amino-1-phenylpropane, 2-amino-1-(p-hydroxyphenyl) propane, 2-amino-1-(p-trifluoromethylphenyl)propane, 2-amino-1-cyclohexylpropane, 2-amino-6-methylheptane, 2-aminoheptane, 2-amino-4-methylhexane, 1-(4-methylphenyl)ethylamine, 1-(4-methoxyphenyl) ethylamine, 1-(3-methoxyphenyl)ethylamine, 1-aminotetralin, trans-1-amino-2-benzyloxycyclopentane and trans-1-amino-2-benzyloxycyclohexane.

Particularly preferred amines I are 2-butylamines and primary β-alkoxy-alkylamines, preferably primary β-alkoxyalkylamines in which $R^1$=1-alkoxy-substituted alkyl, in particular 1-($C_{1-20}$-alkoxy, as defined above)-substituted $C_{1-20}$-alkyl (as defined above), $R^2$=alkyl, in particular $C_{1-20}$-alkyl (as defined above), and $R^3$=H.

Examples are 1-methoxy-2-aminopropane (MOIPA), 2-amino-3-methylbutane and 2-amino-3,3-dimethylbutane.

In a particular variant, the optically active amine I used in the process of the present invention is one which has been obtained by cleavage of an amide which is derived from this optically active amine and is obtained in the preparation of a particular enantiomer of I (based on the asymmetric carbon atom in I) by (a) enantioselective acylation of the racemic amine I by means of an ester whose acid component bears a fluorine, nitrogen, phosphorus, oxygen or sulfur atom in a vicinal position relative to the carbonyl carbon in the presence of a hydrolase and (b) separation of the resulting mixture of optically active amine I and amide.

In a further particular variant, the optically active amine I used in the process of the present invention is one which has been obtained in the preparation of a particular enantiomer of I (based on the asymmetric carbon atom in I) by (a) enantioselective acylation of the racemic amine I by means of an ester whose acid component bears a fluorine, nitrogen, phosphorus, oxygen or sulfur atom in a vicinal position relative to the carbonyl carbon in the presence of a hydrolase, (b) separation of the resulting mixture of optically active amine I and amide and (c) isolation of the other enantiomer of I by cleavage of the amide.

The methods of preparing optically active amines I from the corresponding racemates by (a) enantioselective acylation of the racemic amine I by means of an ester whose acid component bears a fluorine, nitrogen, phosphorus, oxygen or sulfur atom in a vicinal position relative to the carbonyl carbon in the presence of a hydrolase, (b) separation of the resulting mixture of optically active amine I and amide and (c) isolation of the other enantiomer of I by cleavage of the amide are described in WO 95/08636 and WO 96/23894.

The hydrolase is, for example, a lipase, in particular a microbial lipase. The ester is, for example, a $C_{1-12}$-alkyl ester of a $C_{1-4}$-alkoxyacetic acid, e.g. ethyl methoxyacetate.

The cleavage of the amide derived from the optically active amine I with retention of the chiral center can be achieved by hydrolysis, for example by hydrolysis in the presence of a polyol or an amino alcohol and an alkali metal hydroxide or alkaline earth metal hydroxide as described in WO 97/10201.

These particular process variants are particularly economical, since after the preparation of the desired enantiomer of the amine I, e.g. as described in WO 95/08636 or WO 96/23894, the remaining, undesired enantiomer of I is racemized by means of the process of the present application and is reused in the process for preparing the desired enantiomer of I, e.g. as described in WO 95/08636 or WO 96/23894. This makes it possible to obtain a total of more than 50% of the desired enantiomer from the racemic amine I. (On this subject, see also page 1 of the description, 2nd paragraph).

EXAMPLES

Example 1

Production of the Catalyst

1a) Preparation of the Support 450 g of $Al(NO_3)_3 \cdot 9H_2O$ were added to 649 g of a well-stirred aqueous solution of zinc nitrate having a zinc content of 14.5% by weight and the mixture was made up to a volume of 1.25 l with water in order to bring the aluminum salt into solution (solution A). In a separate vessel, 474 g of anhydrous sodium carbonate were dissolved in water and the solution was made up to 2 l with water (solution B).

Solution A and solution B were heated to 50° C. and fed via separate lines into a precipitation vessel containing a well stirred solution of 20 g of $NaHCO_3$ in 350 ml of water which had likewise been heated to 50° C. The pH was brought to 6.8 within about 3 minutes by appropriate adjustment of the rates of addition of the solutions A and B. While maintaining a constant pH of 6.8 and a temperature of 50° C., all of solution A was reacted with sodium carbonate. The suspension formed in this way was subsequently stirred for another 3 hours, with the pH being maintained at 6.8 by occasional addition of dilute nitric acid. The suspension was filtered and washed with distilled water until the nitrate content of the washings was less than 10 ppm. The filter cake was dried at 120° C. for 16 hours and subsequently calcined at 425° C. for 1 hour.

1b) Production of the Catalyst

A mixture of 432 g of a copper nitrate solution which had been acidified with nitric acid and had a copper content of 15.5% by weight and 95 g of a zinc nitrate solution which had been acidified with nitric acid and had a zinc content of 14.5% by weight was diluted to 500 ml with water and heated to 70° C. While stirring, 25.1 g of the above-described pulverulent calcined support were slowly added over a period of about 5 minutes and the milky suspension obtained in this way was stirred for 15 minutes (suspension C).

In a separate vessel, 474 g of anhydrous sodium carbonate were dissolved in water and the solution was made up to 2 l with water and heated to 70° C. (solution D). Suspension C and solution D were fed via separate lines into a precipitation vessel which was provided with a stirrer and contained 350 ml of water which had been heated to 70° C. The pH was brought to 7.4 by appropriate adjustment of the rates of addition of the suspension C and solution D.

While maintaining a constant pH of 7.4 and a temperature of 70° C., all of the suspension C was reacted with sodium carbonate. The suspension formed in this way was subsequently stirred for another 2 hours, with the pH being maintained at 7.4 by occasional addition of dilute nitric acid or sodium carbonate solution D. The suspension was filtered and washed with distilled water until the nitrate content of the washings was less than 10 ppm.

The filter cake was dried at 120° C. for 16 hours and subsequently calcined at 430° C. for 1 hour. The brownish black catalyst powder obtained in this way was mixed with 1.5% by weight of graphite and 5% by weight of copper powder (grade FFL No. 10914 from Norddeutsche Affinerie, having a BET surface area of 0.23 $m^2/g$ and a particle size distribution in which 92% of the particles are in the size range from 10 to 100 μm) and pressed to form pellets having a diameter of 3 mm and a height of 3 mm. The pellets were finally calcined at 330° C. for 1 hour.

The catalyst produced in this way had the chemical composition 66% of CuO, 24% of ZnO, 5% of $Al_2O_3$ and 5% of Cu (figures in % by weight).

Example 2

Continuous Racemization of (S)-MOIPA

In a tube reactor (40×3500 mm) heated by means of oil, 1000 ml (bed volume) of the catalyst from Example 1 were introduced on top of a bed of 250 ml of V2A rings and subsequently covered with 3000 ml of V2A rings. The catalyst was activated firstly with a mixture of hydrogen and nitrogen (5:95% by volume) and subsequently with pure hydrogen at 180–220° C. At 230° C. and 16 bar (absolute) of hydrogen, 200 ml/h of (S)-MOIPA (purity according to GC: 95.4% of (S)-MOIPA) were fed into the reactor together with sufficient ammonia for the proportion of ammonia in the circulating gas to be about 20% by volume. The fresh hydrogen gas and the circulating gas had a flow of 300 standard l/h and 6.4 standard $m^3$/h respectively (standard l=standard liters, standard $m^3$=standard cubic meters: volume converted to S.T.P.). After steady-state operation had been attained, a sample was taken from the output from the reactor and analyzed by gas chromatography. This indicated a racemization yield of 94% and a degree of racemization of 96.2% (51.9% of (S)- and 48.1% of (R)-MOIPA).

The GC conditions employed in the examples for the analysis of the output from the reactor were: 30 m RTX-5 amine 0.32 mm, 1.5 μm, 80° C./4 min.—10 min.—280° C./5 min.

The GC method used in the examples for determining the enantiomeric excess of MOIPA was as follows:

MOIPA is acetylated by means of acetic anhydride on an analytical scale. The crude product is analyzed by GC.

| GC conditions: | instrument: HP-5890-II |
| --- | --- |
| | column: 20 m Chiraldex G-TA (from Astec) |
| | carrier gas: helium |
| | prepressure: 65 kPa |
| | injector temperature: 250° C. |
| | detector: FID |

-continued

| | |
|---|---|
| detector temperature: | 275° C. |
| amount injected: | 1 µl |
| temperature program: | 125° C. isothermal |
| retention times: | MOIPA (acetamide): (S)-enantiomer: 4.5 min., |
| (R)-enantiomer: | 5.3 min. |

Examples 3–8

Continuous Racemization of (S)-MOIPA

One of the catalysts 1–5 (see below) in reduced and passivated form was installed in a continuously operated laboratory apparatus (60 ml tube reactor) without recirculation and was reduced at 200° C. under a hydrogen atmosphere for 6 hours (atmospheric pressure). Hydrogen was then passed through the reactor at a flow rate of 18 standard l/h under a pressure of 16 bar. After the abovementioned reaction conditions had been set, ammonia was introduced (at a weight hourly space velocity of 0.2 kg/l*h: 17 g of ammonia; at a weight hourly space velocity of 0.4 kg/l*h: 34 g of ammonia; at a weight hourly space velocity of 0.46 kg/l*h: 38 g of ammonia). The output was depressurized in a separator and analyzed by gas chromatography.

The Following Catalysts Were Used (Figures in % by Weight)

Catalyst 1: 53% CuO, 5% Cu, 42% $TiO_2$, in accordance with DE-A-198 59 776
Catalyst 2: 53% CuO, 47% $Al_2O_3$, in accordance with EP-A-691 157, page 5, line 55, to page 6, line 11
Catalyst 3: 70% Cuo, 24.5% ZnO, 5.5% $Al_2O_3$, in accordance with Example from U.S. Pat. No. 3,923,694
Catalyst 4: 45% CuO, 10% NiO, 45% $Al_2O_3$, in accordance with EP-A-514 692
Catalyst 5: 66% Cuo, 24% ZnO, 5% $Al_2O_3$, 5% Cu powder, in accordance with Example 1

Results

| | | | | | GC analyses | | |
|---|---|---|---|---|---|---|---|
| Example No. | Catalyst | WHSV in kg/l*h | Temp. in ° C. | ee in % | MOIPA RT = 4.7 | RT = 5.9 | Dimer RT = 12.6 |
| 3 | 1 | 0.46 | 200 | 88.6 | 98.2 | 0.2 | 0.9 |
| 4 | 2 | 0.2 | 200 | 83 | 97.7 | 0.3 | 1 |
| 5 | 3 | 0.2 | 200 | 0 | 84.35 | 2.01 | 12.59 |
| 6 | 4 | 0.2 | 200 | 0 | 68.9 | 1.87 | 26.67 |
| 7 | 5 | 0.2 | 220 | 0.2 | 80.68 | 2.36 | 10.12 |
| 8 | 5 | 0.4 | 220 | 1.2 | 89.24 | 1.32 | 8.44 | kg/l*h = kg of MOIPA in the reactor feed per liter of catalyst (bed volume) and per hour
RT = retention time in the GC in min.
The figures for the composition of the output from the reactor (GC analysis) are in GC % by area
Dimer = diamine (secondary amine)

Examples No. 3, 4 and 6 (catalysts 1, 2 and 4) are Comparative Examples

The examples show that for (S)-MOIPA under the reaction conditions employed, the Cu catalysts 1 and 2 gave degrees of racemization (ee values: 83 and 88.6%, respectively) which were in need of improvement.

Although use of the nickel-containing Cu catalyst 4 gave complete racemization (ee: 0%), the racemization yield (racemate yield) was in need of improvement (only 68.9 GC % by area of MOIPA and a high dimer content of 26.67 GC % by area in the output).

The Cu/Zn catalysts 3 and 5 according to the present invention gave a high space-time yield and also a high degree of racemization and a high racemization yield.

Example 9

(Combined Process): Continuous Racemization of (S)-MOIPA and In situ Amination of 1-methoxy-2-propanol In a tube reactor (48×2100 mm) heated by means of oil, 1000 ml of the catalyst from Example 1 were introduced on top of a bed of 60 ml of V2A rings and subsequently covered with 1330 ml of V2A rings. The catalyst was activated firstly with a mixture of hydrogen and nitrogen and subsequently with pure hydrogen at 180–220° C. At 230° C. and 16 bar (absolute) of hydrogen, 500 ml/h of a mixture of 1-methoxy-2-propanol and (S)-MOIPA in a weight ratio of 4:1 were fed into the reactor together with sufficient ammonia for the proportion of ammonia in the circulating gas to be about 40% by volume. The fresh hydrogen gas and the circulating gas had a flow of 300 standard l/h and 6.4 standard $m^3/h$ respectively. After steady-state operation had been attained, a sample was taken from the output from the reactor and analyzed by gas chromatography. This indicated an (R,S)-MOIPA selectivity of 91% and a degree of racemization of 99.8% [49.9% of (R)-MOIPA, 50.1% of (S)-MOIPA] at a conversion of 99%.

Example 10

Comparative Example

Experiment on the racemization of (R)-MOIPA by a method analogous to that of DE-A-29 03 589

10 g of (R)-MOIPA (112 mmol), 70 ml of tetrahydrofuran and 1 g of Raney cobalt were placed in a 0.3 l autoclave. A pressure of 20 bar was set by means of hydrogen. The autoclave was heated to 160° C. and the H-pressure was increased to 50 bar. After 12 hours under these conditions, the mixture was cooled to room temperature, the catalyst was filtered off and the tetrahydrofuran was taken off on a rotary evaporator. The weight of residue was 2.5 g.

Determination of the enantiomeric excess (ee) by HPLC analysis: 4.8%

(S)-MOIPA=47.6% by area
(R)-MOIPA=52.4% by area

| GC analysis [% by area]: | |
|---|---|
| tetrahydrofuran: | 0.2 |
| methoxyisopropanol: | 2.2 |

-continued

| GC analysis [% by area]: | |
|---|---|
| (R)- + (S)-MOIPA: | 68.3 |
| octylamine: | 3.7 |
| octanol: | 10.0 |
| total unknown compounds: | 15.6 |
| degree of racemization: | 90% |
| racemate yield: | 61% |

Example 11

Comparative Example

Experiment on the racemization of (S)-3,3-dimethyl-2-aminobutane (pinacolylamine) by a method analogous to that of DE-A-29 03 589

10 g of (S)-pinacolylamine (99% ee) were mixed with 60 g of THF and 1 g of Raney cobalt in a 0.3 l tube autoclave and stirred for 12 hours under a hydrogen atmosphere at a pressure of 50 bar and a temperature of 165° C.

The contents of the reactor were then cooled to room temperature, separated from the catalyst and the ratio of enantiomers was determined by means of a chiral HPLC column.

Enantiomeric excess: 99%

GC analysis of the output (ammonia- and water-free) in GC % by area:

| pinacolone | 0.1 |
|---|---|
| pinacolylamine | 99.2 |
| pinacolole | 0.5 |
| others | 0.2 |
| degree of racemization: | 0% |
| racemate yield: | 99.2% |

Example 12

Amination of 1-methoxy-2-propanol

In a tube reactor (48×2100 mm) heated by means of oil, 1000 ml of the catalyst from Example 1 were introduced on top of a bed of 60 ml of V2A rings and subsequently covered with 1330 ml of V2A rings. The catalyst was activated with a mixture of hydrogen and nitrogen or with pure hydrogen at 180–220° C. At 220° C. and 16 bar (absolute) of hydrogen, 200 ml/h of 1-methoxy-2-propanol were fed into the reactor together with sufficient ammonia for the proportion of ammonia in the circulating gas to be about 40% by volume. The fresh hydrogen gas and the circulating gas had a flow of 300 standard l/h and 6.4 standard m³/h respectively. After steady-state operation had been attained, a sample was taken from the output from the reactor and analyzed by gas chromatography. This indicated an (R,S)-MOIPA selectivity of 94.6% at a conversion of 99.4%.

We claim:

1. A process for racemizing optically active amines of the formula I

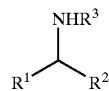

(I)

where $R^1$ and $R^2$ are different and $R^1$, $R^2$, $R^3$ are alkyl, cycloalkyl, arylalkyl, aryl, heteroaryl and heterocyclic radicals and $R^3$ may also be hydrogen (H), with the radicals being able to bear substituents selected from the group consisting of alkyl, cycloalkyl, alkoxy, aryloxy, amino, alkylamino and dialkylamino, by reacting the optically active amine I in the presence of hydrogen and a hydrogenation or dehydrogenation catalyst at elevated temperature, wherein the catalyst comprises the active components copper, zinc oxide and zinc-aluminum spinel and a support material.

2. A process as claimed in claim 1, wherein the catalyst comprises an oxidic support material selected from the group consisting of aluminum oxide, silicon dioxide, titanium dioxide, zirconium dioxide, magnesium oxide, iron oxide and cerium dioxide, or carbon or a mixture thereof.

3. A process as claimed in claim 1, wherein the catalyst after drying and before activation with a reducing agent comprises from 20 to 90% by weight of oxygen-containing compounds of copper, calculated as CuO, from 9 to 60% by weight of oxygen-containing compounds of zinc, calculated as ZnO, and from 1 to 60% by weight of aluminum oxide, calculated as $Al_2O_3$, in each case based on the total weight of all oxidic constituents of the catalyst.

4. A process as claimed in claim 1, wherein the catalyst after drying and before activation with a reducing agent comprises from 40 to 85% by weight of oxygen-containing compounds of copper, calculated as CuO, from 13 to 40% by weight of oxygen-containing compounds of zinc, calculated as ZnO, and from 2 to 35% by weight of aluminum oxide, calculated as $Al_2O_3$, in each case based on the total weight of all oxidic constituents of the catalyst.

5. A process as claimed in claim 1, wherein the catalyst after drying and before activation with a reducing agent comprises the constituents oxygen-containing compounds of copper, oxygen-containing compounds of zinc and aluminum oxide in a combined amount of at least 80% by weight, based on the total weight of all oxidic constituents of the catalyst.

6. A process as claimed in claim 1, wherein the reaction is carried out at from 100 to 300° C.

7. A process as claimed in claim 1, wherein the reaction is carried out at pressures of from 0.1 to 30 MPa.

8. A process as claimed in claim 1, wherein the reaction is carried out in the presence of the amine of the formula $R^3NH_2$ in which the radical $R^3$ corresponds to the radical $R^3$ of the optically active amine I.

9. A process as claimed in claim 8, wherein the secondary alcohol of the formula II and/or the unsymmetrical ketone of the formula III

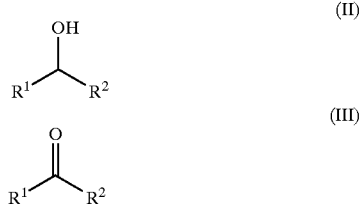

in which the radicals $R^1$ and $R^2$ correspond to the radicals $R^1$ and $R^2$ of the amine I, are/is reacted simultaneously in situ to form the racemic amine I.

10. A process as claimed in claim 1, wherein the optically active amine I used is primary β-alkoxyalkylamine in which $R^1$=1-alkoxy-substituted alkyl, $R^2$=alkyl and $R^3$=H.

11. A process as claimed in claim 10, wherein the optically active amine I used is 1-methoxy-2-propylamine.

12. A process as claimed in claim 1, wherein the optically active amine I used is 3-methyl-2-butylamine or 3,3-dimethyl-2-butylamine.

13. A process as claimed in claim 9, wherein 1-methoxy-2-propylamine is used as optically active amine I and 1-methoxy-2-propanol is used as secondary alcohol II.

14. A process as claimed in claim 1, wherein the optically active amine I has been obtained by cleavage of an amide which is derived from this optically active amine and is obtained in the preparation of a particular enantiomer of I by (a) enantioselective acylation of the racemic amine I by means of an ester whose acid component bears a fluorine, nitrogen, phosphorus, oxygen or sulfur atom in a vicinal position relative to the carbonyl carbon in the presence of a hydrolase and (b) separation of the resulting mixture of optically active amine I and amide.

15. A process as claimed in claim 1, wherein the optically active amine I has been obtained in the preparation of a particular enantiomer of I by (a) enantioselective acylation of the racemic amine I by means of an ester whose acid component bears a fluorine, nitrogen, phosphorus, oxygen or sulfur atom in a vicinal position relative to the carbonyl carbon in the presence of a hydrolase, (b) separation of the resulting mixture of optically active amine I and amide and (c) isolation of the other enantiomer of I by cleavage of the amide.

* * * * *

UNITED STATES PATENT AND TRADEMARK OFFICE
CERTIFICATE OF CORRECTION

PATENT NO. : 6,548,704 B2
DATED : April 15, 2003
INVENTOR(S) : Funke et al.

It is certified that error appears in the above-identified patent and that said Letters Patent is hereby corrected as shown below:

Column 17,
Line 2, after "is" insert -- a --.

Signed and Sealed this

Eighth Day of July, 2003

JAMES E. ROGAN
*Director of the United States Patent and Trademark Office*